United States Patent
Bashar et al.

(10) Patent No.: US 7,435,576 B2
(45) Date of Patent: Oct. 14, 2008

(54) FILTER SNAPPER

(75) Inventors: Reza Bashar, San Diego, CA (US); Dale A. Camper, San Diego, CA (US)

(73) Assignee: Gen-Probe Incorporated, San Diego, CA (US)

( * ) Notice: Subject to any disclaimer, the term of this patent is extended or adjusted under 35 U.S.C. 154(b) by 663 days.

(21) Appl. No.: 10/951,875

(22) Filed: Sep. 29, 2004

(65) Prior Publication Data

US 2005/0069973 A1    Mar. 31, 2005

Related U.S. Application Data

(60) Provisional application No. 60/506,733, filed on Sep. 30, 2003.

(51) Int. Cl.
*C12M 1/34* (2006.01)
*C12M 3/00* (2006.01)
(52) U.S. Cl. .................. 435/287.3; 100/48; 100/98 R; 435/297.3; 422/101; 422/121
(58) Field of Classification Search ............. 435/287.3, 435/297.5; 210/451, 454; 422/101, 121; 100/48, 98 R
See application file for complete search history.

(56) References Cited

U.S. PATENT DOCUMENTS

| 4,235,164 A | 11/1980 | Allen et al. |
| 4,265,170 A | 5/1981 | Schulze, Jr. |
| 4,316,410 A * | 2/1982 | Davis, Jr. .................. 100/48 |
| 4,463,670 A | 8/1984 | Thomas |
| 4,599,941 A | 7/1986 | Johnson et al. |
| 4,614,585 A | 9/1986 | Mehra et al. |

(Continued)

FOREIGN PATENT DOCUMENTS

EP    0463897 A1    1/1992

(Continued)

OTHER PUBLICATIONS

Milliflex® 100 Filtration Funnel, Certificate of Quality, Dec. 2003, Millipore Corporation, Bedford, MA 01730.

(Continued)

*Primary Examiner*—Walter D Griffin
*Assistant Examiner*—Shanta G Doe
(74) *Attorney, Agent, or Firm*—Rothwell, Figg, Ernst & Manbeck, PC; Charles B. Cappellari (57) ABSTRACT

A device for applying an axial compressive force to a fluid contamination detection system comprising a cup joined by a frangible connection to a filter ring, the force being sufficient to break the frangible connection and collapse a portion of the ring into the cup without damaging the ring. The device includes a stop element and a platform and an actuating mechanism for reciprocally moving the platform relative to the stop element. In a first position, the distance between the platform and the stop element is greater than the axial length of the detection system when the cup and the filter ring of the funnel are connected to each other, and in a second position, the distance between the platform and the stop element is less than the axial length of the detection system when the cup and the filter ring of the funnel are connected to each other.

18 Claims, 5 Drawing Sheets

U.S. PATENT DOCUMENTS

| | | | |
|---|---|---|---|
| 4,696,227 A * | 9/1987 | Van Buskirk | 100/90 |
| 4,821,969 A | 4/1989 | Fox et al. | |
| 5,202,262 A | 4/1993 | Lemonnier | |
| 5,297,479 A * | 3/1994 | Negus | 100/48 |
| 5,308,483 A | 5/1994 | Sklar et al. | |
| 5,383,397 A * | 1/1995 | Battles et al. | 100/51 |
| 5,905,038 A | 5/1999 | Parton | |
| 6,358,730 B1 | 3/2002 | Kane | |
| 2002/0083851 A1 * | 7/2002 | Gragg | 100/902 |

FOREIGN PATENT DOCUMENTS

| | | |
|---|---|---|
| WO | WO 0148142 A1 | 7/2001 |
| WO | WO 0159157 A2 | 8/2001 |

OTHER PUBLICATIONS

EPO Office Action, European Patent Application No. 04 789 432.4, Oct. 9, 2006.

PCT Search Report, International Application No. PCT/US04/032326, Feb. 4, 2005.

PCT Written Opinion, International Application No. PCT/US04/032326, Feb. 4, 2005.

* cited by examiner

FILTER SNAPPER

The present application claims the benefit of U.S. Provisional Application No. 60/506,733 filed Sep. 30, 2003, the disclosure of which is hereby incorporated by reference.

BACKGROUND OF THE INVENTION

1. Field of the Invention

The present invention relates to a device and a method for separating a filter ring component from a fluid-holding reservoir component of a funnel with minimal operator effort.

2. Description of the Background Art

In certain sterile operations (e.g., laboratory and manufacturing procedures), it is necessary to regularly monitor fluid supplies, such as water supplies, used in such procedures to ensure that they do not contain unacceptable levels of contaminants, such as biological contaminants. Typical biological contaminants include bacteria and fungi. One method of monitoring fluid supplies involves passing a specified sample volume of a fluid from a fluid supply through a filter, positioning the filter on a contained biological growth medium (e.g., an agar plate), enclosing and incubating the contained biological growth medium, and then observing the level of the biological growth at prescribed intervals of time. Specialized filtration testing systems are manufactured for this purpose.

Figure 1:
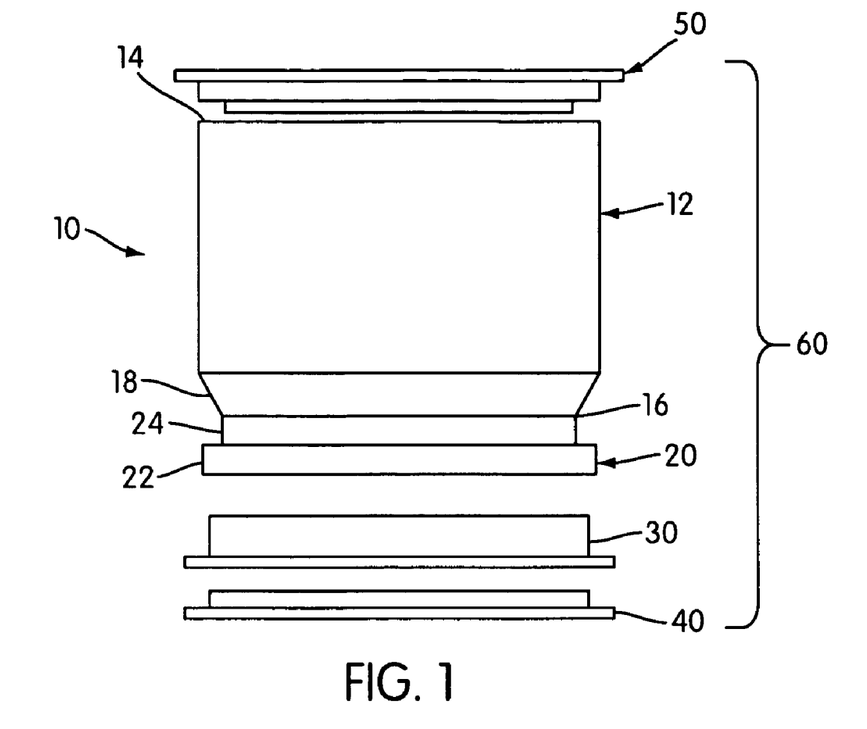
FIG. 1 is an exploded view, shown in side elevation, of components of a conventional filtration testing system.
Figure 2:
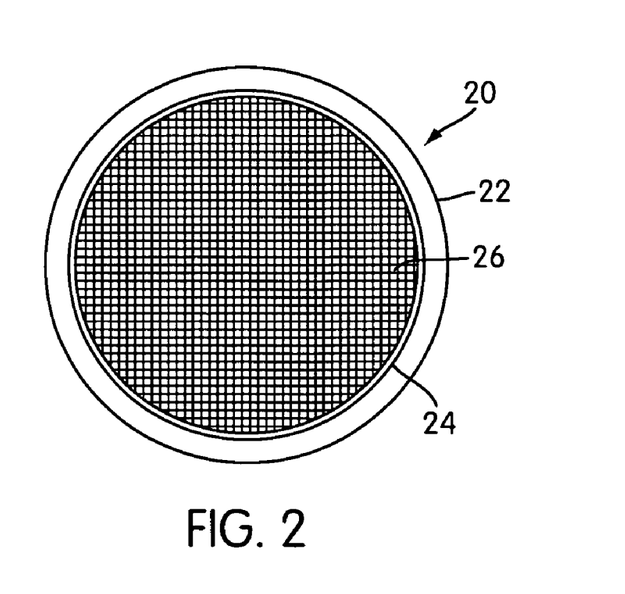
FIG. 2 is a plan view of a filter ring of the filtration testing system of FIG. 1.
Figure 3:
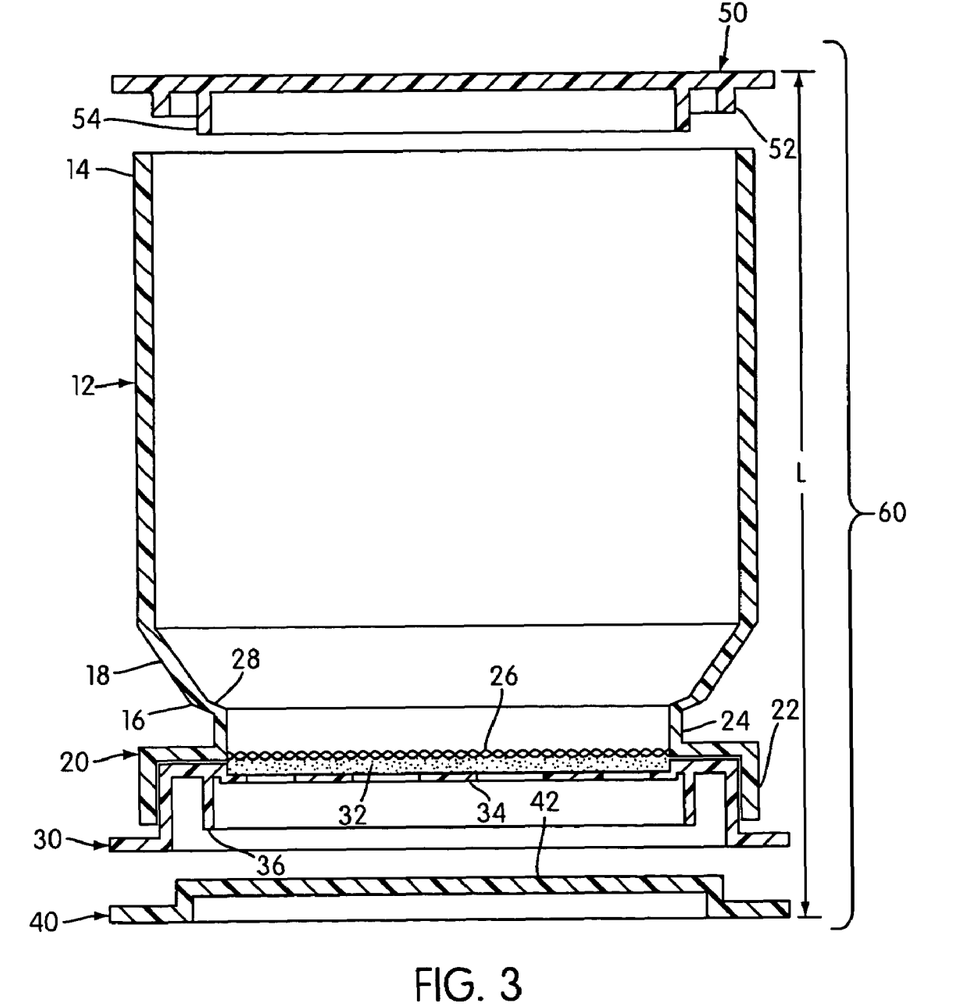
FIG. 3 is an exploded view, shown in vertical cross-section, of components of the filtration testing system of FIG. 1.

One such filtration testing system is illustrated in FIGS. 1-3. This filtration testing system 60 includes a funnel 10 that includes a fluid-holding cup 12 for receiving an amount of a fluid to be tested and a filter ring 20 having a filter 26 (e.g., a filtration mesh) disposed across its opening. More specifically, the cup 12 includes a top end 14, a bottom end 16 having a width (e.g., diameter) less than that of the top end 14, and a frusto-conical section 18. The filter ring 20 includes a wide portion 22 and a narrow portion 24 having a width (e.g., diameter) less than that of the wide portion 22. The filter 26 is disposed generally between the wide portion 22 and the narrow portion 24. The filter ring 20 is frangibly attached, at frangible connection 28, to the bottom end 16 of the cup 12. The frangible connection 28 is constructed and arranged to break upon application to the funnel 10 of a sufficient compressive axial force, thereby permitting the narrow section 24 of the filter ring to collapse into the bottom end 16 of the cup 12. After the frangible connection 28 is broken, the filter ring 20 and cup 12 can be separated from each other.

The system 60 further includes a growth medium plate 30 (e.g., an open-ended agar plate), a lower cover plate 40, and an upper cover plate 50.

The filter ring 20 can be connected to the growth medium plate 30. The growth medium plate 30 has a size and shape that conforms to the interior of the wide portion 22 of the filter ring 20, permitting the plate 30 to be snugly inserted into the wide portion 22 as shown FIG. 3. The growth medium plate 30 includes a layer of growth medium 32 supported by a lattice structure 34. An inner extension 36 is preferably circular and projects away from the growth medium 32 and lattice structure 34, generally encircling the growth medium 32 and the lattice structure 34.

The lower cover plate 40 has a size and shape that conforms to the interior of the growth medium plate 30, permitting the lower cover plate 40 to be snugly inserted into the growth medium plate 30 as shown FIG. 3. When the lower cover plate 40 is inserted into the plate 30, a top surface 42 of the lower cover plate 40 makes contact with the inner extension 36, thereby forming a partial enclosure surrounding the growth medium 32 and the lattice structure 34.

The upper cover plate 50 includes a first extension 52 and a second extension 54. The first extension 52 has a size and shape that permits that upper cover plate 50 to be secured to the top end 14 of cup 12 by inserting the first extension 52 into the cup 12. After the cup 12 and the filter ring 20 have been separated from each other, the second extension 54 has a size and shape that permits the upper cover plate 50 to be secured to the narrow portion 24 of the filter ring 20 by inserting the second extension 54 into the narrow portion 24.

The funnel 10, in combination with the growth medium plate 30, the upper cover plate 50, and the lower cover plate 40, make up the fluid contamination detection system 60 having an overall axial length L. A suitable system of the type shown in FIGS. 1-3 is the Milliflex™ HAWG 0.45 μM, sterilized filtration funnel available from the Millipore Corporation, Bedford, Mass. (Cat. No. MXHAWG124). This system may further include, for example, a Prefilled Milliflex™ Cassette containing tryptic soy agar available from the Millipore Corporation (Cat. No. MXSMCTS48).

In a conventional fluid contamination detection system and procedure, the funnel 10 is placed on a suction mechanism, or vacuum suction, (such as the Milliflex™ Sensor II automatic vacuum available from the Millipore Corporation (Cat. No. MXP520015)), a prescribed volume of fluid (e.g., about 10 mL) is then poured into the cup 12, and the fluid contents of the cup 12 are drawn through the filter 26 of the filter ring 20. After the fluid has been drawn through the filter 26, the growth medium plate 30 is joined to the filter ring 20 so that the growth medium 32 contained within the growth medium plate 30 contacts the filter 26 of the filter ring 20. Thereafter, the filter ring 20 and growth medium plate 30 are separated from the cup 12. To separate the filter ring 20 and growth medium plate 30 combination from the cup 12, the filter 10 and growth medium plate 30 are manually squeezed between the palms and fingers of an operator's hands to apply an axial compressive force to the filter 10 and growth medium plate 30 that is sufficient to break the frangible connection 28 joining the cup 12 and ring 20 so that the narrow portion 24 of the filter ring 20 collapses into the bottom end 16 of the cup 12. The filter ring 20 and growth medium plate 30 are then separated from the cup 12, and the upper cover plate 50 is joined to the open end of the filter ring 20 before incubating the enclosed growth medium plate 30 at a temperature of about 37° C.

It is generally desirable to perform this procedure in a laminar flow hood in order to limit exposure of the filter to airborne contaminants that could interfere with fluid monitoring test results. During the incubation phase, the growth medium plate 30 is examined at prescribed time intervals, e.g., 24, 48, and 72 hours, and the number of colonies that have formed on the plate (the bioburden) is determined. Such a fluid contamination detection system is especially important for the clinical diagnostics industry, where the presence of biological contaminants in fluids used to manufacture reagents for commercial test kits could affect the results of assays performed using those test kits.

A problem with the fluid contamination detection system and procedure described above is that laboratory and manufacturing facilities might have to perform dozens of fluid contamination detection tests in a day. As a consequence, an operator may be required to repeatedly apply a manual force with their hands to separate filter ring 20 and growth medium plate 30 combinations from corresponding cups 12, often resulting in discomfort to the operator's hands or, more seriously, causing repetitive stress injuries, such as carpal tunnel syndrome. Accordingly, there is a need for a device and method that overcome the problems associated with isolating filter ring 20 and growth medium plate 30 combinations in traditional detection systems.

SUMMARY OF THE INVENTION

The present invention provides a novel solution to the repetitive stress problems associated with conventional methods of testing fluids for the presence of contaminants.

Thus, one aspect of the present invention is embodied by a device for applying an axial compressive force to a fluid contamination detection system comprising a funnel in order to break a frangible connection joining first and second members of the funnel. The device includes a stop element, a movable platform supported relative to a base, and an actuating mechanism. The platform is disposed in an opposed, spaced-apart relationship relative to the stop element. The platform is movable relative to the stop element between a first position in which the platform is spaced-apart from the stop element by a distance greater than the axial length of the detection system and a second position in which the platform is spaced-apart from the stop element by a distance less than the axial length of the detection system. The actuating mechanism causes movement of the platform between the first and second positions. The platform is movable from the first position to the second position during which movement a portion of the detection system contacts the stop element, resulting in an axial compressive force that breaks the frangible connection joining the first and second members of the funnel.

Another aspect of the invention is embodied by a filter snapper system which includes a fluid contamination detection system comprising a funnel having first and second members joined to each other by a frangible connection in combination with the device for applying an axial compressive force to the fluid contamination detection system for breaking the frangible connection as described above.

Another aspect of the invention is embodied by a method for separating first and second members of a funnel joined to each other by a frangible connection using the device for applying an axial compressive force to the fluid contamination detection system for breaking the frangible connection as described above. The method comprises the steps of placing the funnel on the platform of the device while the platform is in the first position, activating the actuating mechanism, thereby causing the platform to move until a portion of the funnel engages the stop element, applying an axial compressive force to the funnel sufficient to break the frangible connection without damaging the funnel, and separating the first and second members of the funnel from each other.

Another aspect of the invention is embodied by a method for detecting the presence of biological contaminants in a fluid. A predetermined amount of a fluid is provided to a funnel which includes a first member defining a fluid reservoir for receiving the fluid, a second member joined to the first member by a frangible connection, and a filter, which is adapted to trap biological contaminants present in the fluid, disposed on the second member. Fluid is passed from the first member of the funnel through the filter disposed on the second member, thereby trapping biological contaminants present in the fluid on the filter. A growth medium plate is joined to the second member of the funnel in such a manner that the filter is in contact with a growth medium contained within the growth medium plate. The funnel is positioned on the platform of the device for applying axial force when the platform is in the first position. The actuating mechanism is then activated, thereby causing the platform to move from the first position toward the second position until a portion of the funnel contacts the stop element. An axial compressive force is applied to the funnel, and the force is sufficient to break the frangible connection without damaging the second member of the funnel. The first and second members of the funnel are separated from each other, and the growth medium plate is sealed by placing a cover plate on an open end of the second member of the funnel. The growth medium plate is incubated for a period of time and under conditions sufficient for biological contaminants trapped on the filter to grow; and the filter is examined after incubating to determine the presence or amount of biological contaminants on filter.

Another aspect of the invention is embodied by a method for detecting the presence of biological contaminants in a fluid. The method comprises the steps of providing a predetermined amount of a fluid to a funnel comprising a first member defining a fluid reservoir for receiving the fluid, a second member joined to the first member by a frangible connection, and a filter disposed on the second member and adapted to trap biological contaminants present in the fluid. The fluid is passed from the first member through the filter disposed on the second member, thereby trapping biological contaminants present in the fluid on the filter. The funnel is positioned on a mechanized device constructed and arranged to apply an axial compressive force to the funnel sufficient to break said frangible connection joining the first and second members, and mechanized device is activated, thereby causing the device to apply the axial compressive force to the funnel sufficient to break the frangible connection. After breaking the frangible connection, the first and second members of the funnel are separated from each other. Either before positioning the funnel on the mechanized device or after separating the first and second members from each other, a growth medium plate is joined to the second member of the funnel in such a manner that the filter is in contact with a growth medium contained within the growth medium plate. The second member and the growth medium plate joined thereto are incubated for a period of time and under conditions sufficient for biological contaminants trapped on the filter to grow. The filter is then examined to determine the presence or amount of biological contaminants on the filter.

With these and other objects, advantages and features of the invention that may become hereinafter apparent, the nature of the invention may be more clearly understood by reference to the following detailed description of the invention, the appended claims, and the drawings attached hereto.

BRIEF DESCRIPTION OF THE DRAWINGS

The accompanying drawings, which are incorporated herein and form part of the specification, illustrate various embodiments of the present invention and, together with the description, further serve to explain the principles of the invention and to enable a person skilled in the pertinent art to make and use the invention. In the drawings, like reference numbers indicate identical or functionally similar elements. A more complete appreciation of the invention and many of the attendant advantages thereof will be readily obtained as the same becomes better understood by reference to the following detailed description when considered in connection with the accompanying drawings, wherein.

DETAILED DESCRIPTION OF THE EXEMPLARY EMBODIMENTS

In the following detailed description, reference is made to the accompanying drawings which form a part hereof and in which is shown by way of illustration a specific embodiment in which the invention may be practiced. This embodiment is described in sufficient detail to enable those skilled in the art to practice the invention, and it is to be understood that other embodiments may be utilized and that structural or logical changes may be made without departing from the scope of the present invention. The following detailed description is, therefore, not to be taken in a limiting sense, and the scope of the present invention is defined by the appended claims.

Figure 4:
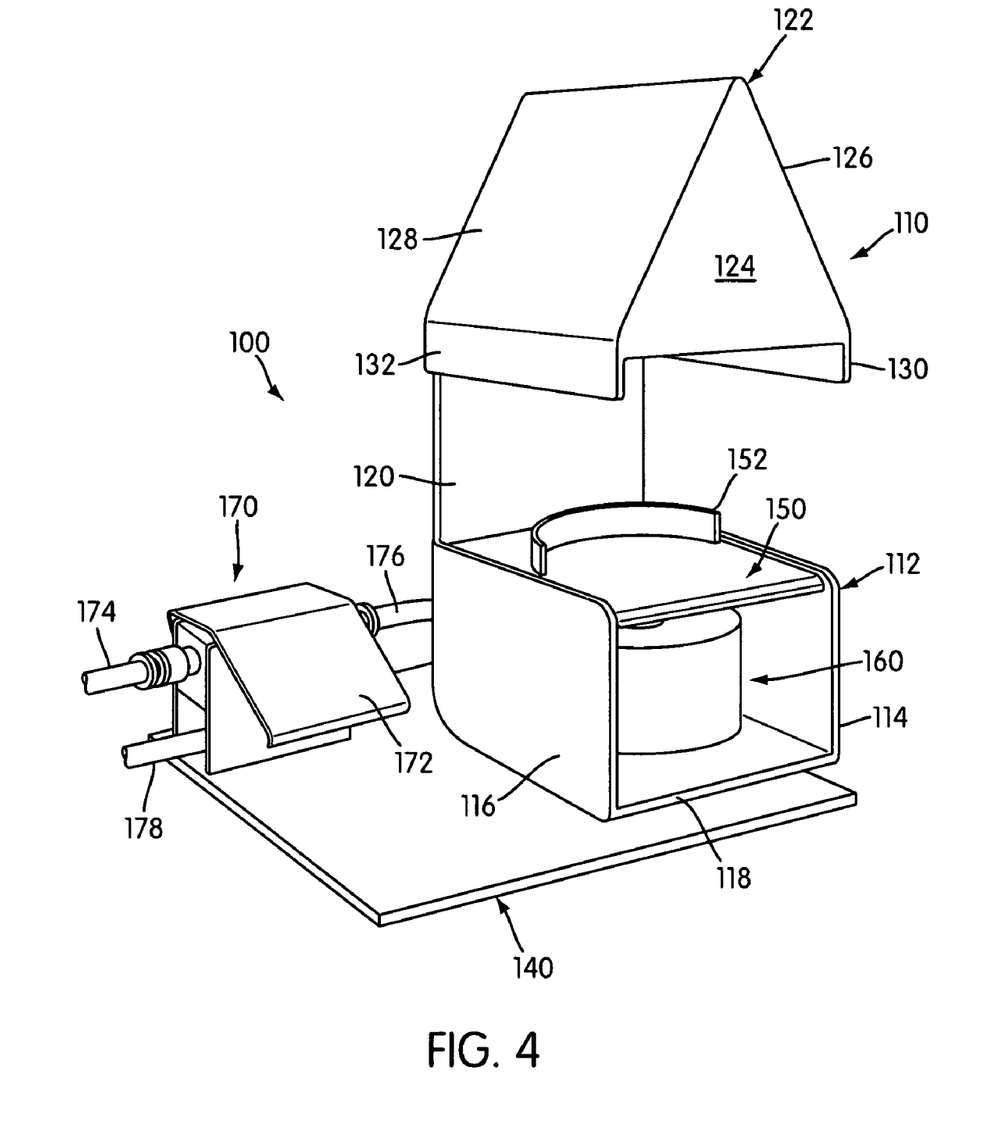
FIG. 4 is a perspective view of a filter snapper device according to an exemplary embodiment of the present invention.
Figure 5:
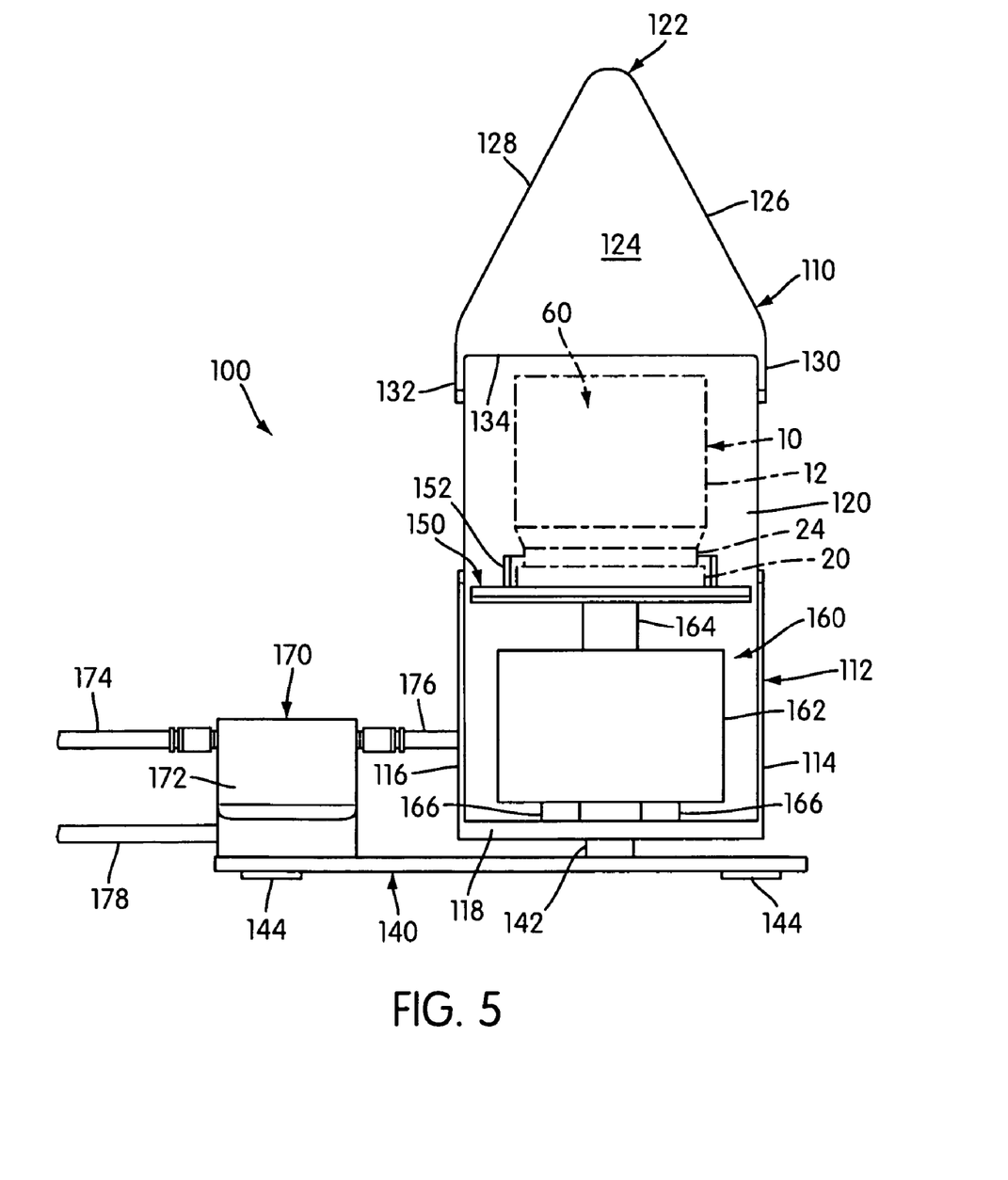
FIG. 5 is a front elevation view of the filter snapper device according to an exemplary embodiment of the present invention in which a movable platform thereof is in a first position with a filtration testing system, shown in phantom, disposed on the movable platform.
Figure 6:
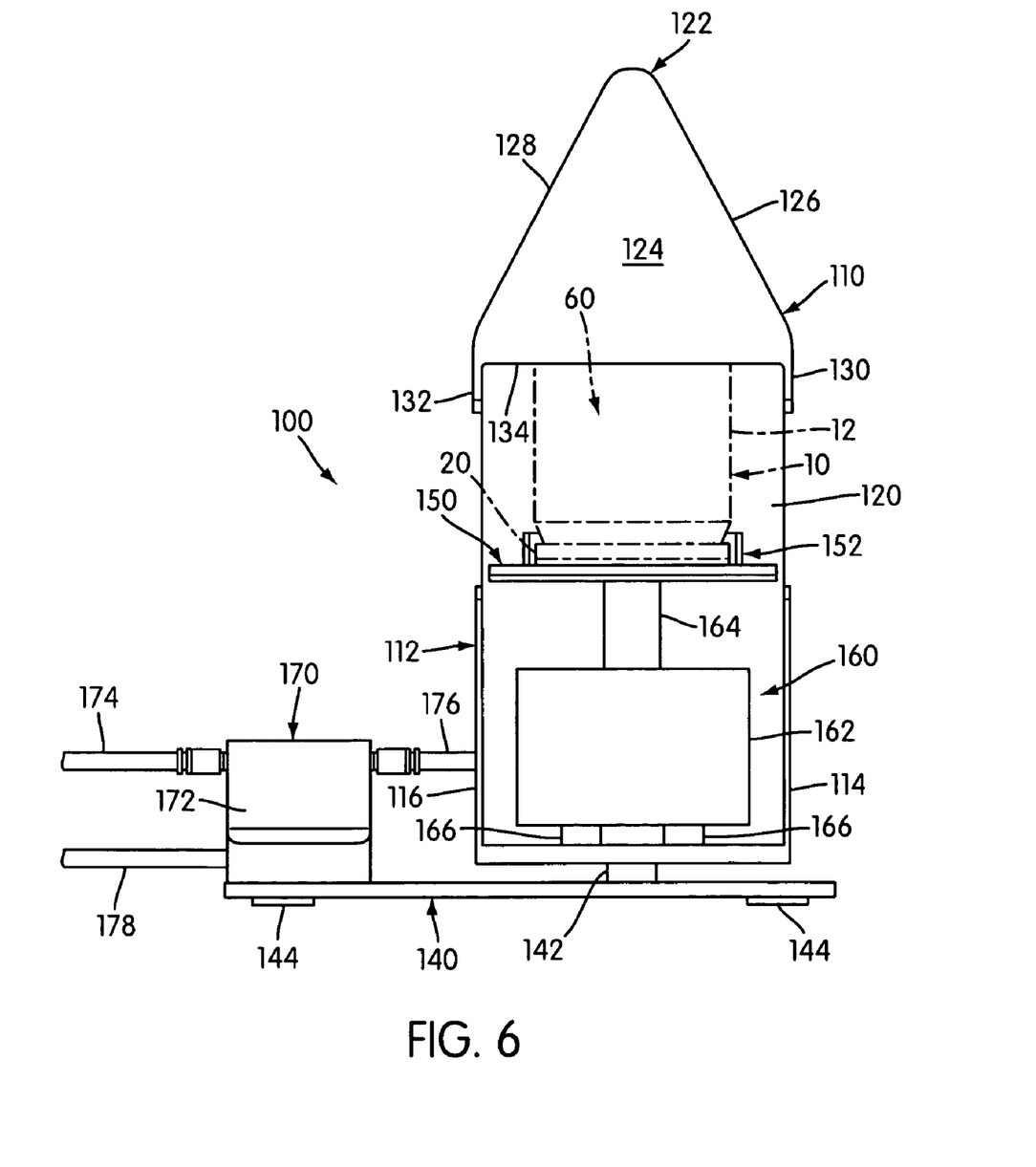
FIG. 6 is a front elevation view of the filter snapper device according to an exemplary embodiment of the present invention in which the movable platform is in a second position.

FIGS. 4-6 show a filter snapper device 100 according to an exemplary embodiment of the present invention. The filter snapper device 100 comprises a housing 110, a movable platform 150 mounted within the housing 110, an actuating mechanism 160 for causing movement of the platform 150, and a valve 170 for controlling the actuating mechanism 160. In the illustrated embodiment, the housing 110 and the valve 170 are mounted to a base plate 140.

The housing 110 has a lower portion 112, a bottom plate 118, a back plate 120, and a hood 122. The lower portion 112 comprises side walls 114, 116. The hood 122 comprises a front plate 124, top plates 126, 128, side walls 130, 132, and a stop surface 134. As shown in FIGS. 5 and 6, the distance between the side walls 130, 132 of the hood 122 is preferably at least as great as the distance between the side walls 114, 116 of the lower portion 112.

In an exemplary embodiment, the housing 110 is shown with the side walls 130, 132 of the hood 122 separated from the side walls 114, 116 of the lower portion 112. The gap between the hood 122 and the lower portion 112 allows easy access for placement or removal of the testing system 60 (shown in phantom in FIGS. 5 and 6) onto or from the platform 150. In an alternate embodiment, the side walls 130, 132 of the hood 122 could extend to and be continuous with the side walls 114, 116 of the lower portion 112.

The housing 110 shown is rectangular with a triangular hood 122 as defined by top plates 126, 128. Alternatively, the housing 110 could be, for example, cylindrical with a conical or hemispherical hood.

In the illustrated embodiment, the top plates 126, 128 are angled with respect to each other and are connected along upper edges thereof to form a triangular hood 122 so that the housing 110 can be placed under a vertical laminar flow hood while causing minimal disruption of the downwardly directed airflow. As shown in FIGS. 5 and 6, the transition from top plate 126 to top plate 128 is preferably rounded, as are the transitions between top plates 126, 128 and side walls 130, 132, respectively. Thus, air flowing downwardly over the housing 110 will experience less disruption than if these transitions were sharply angled.

The platform 150 is attached to the actuating mechanism 160, which in turn is attached to bottom plate 118 of housing 110, and is movable relative to the housing 110 in a reciprocating manner in upward and downward directions. The platform 150 is disposed in an opposed, spaced-apart relationship with respect to the stop surface 134 of the housing 110. The actuating mechanism 160 may comprise a pneumatic actuator, represented in FIGS. 5 and 6 by cylinder 162 and shaft (i.e., pneumatic piston shaft) 164 extending from cylinder 162 and attached to platform 150. The preferred pneumatic actuator for use in the present invention is a single acting, 1½ inch bore, ⅜ inch stroke Flat-1® cylinder available from Bimba Manufacturing Company of Monee, Ill. (Model No. FOS-170.375-3R). The actuator preferably generates a compressive axial force of about 40 pounds-force.

The valve 170 is a 3-way valve, preferably a 3-way air switch available from Mead Fluid Dynamics Inc. of Chicago, Ill. as Model No. MV-5. The valve 170 controls air flow from a pressure line 174 connected to a source of pressurized air (not shown), through the valve 170, to line 176 extending to the pneumatic cylinder 162 coupled to the platform 150. The source of pressurized air could be a wall-mounted conduit connected to a compressor, or it could be a self-contained pressurized air cannister, which would give the device 100 some level of portability and allow it to be operable where a source of pressurized air is not otherwise available. Bleed line 178 allows air flow from the pneumatic cylinder 162.

A trigger plate 172 is pivotally connected to the valve 170 and can be operated by pressing it downwardly. In a neutral position, the pneumatic cylinder 162 is connected to bleed line 178, and the shaft 164 is preferably spring biased into a first, downward position (see FIG. 5). Pressing the trigger plate 172 causes the pneumatic cylinder 162 to be connected to the pressure line 174, thereby pressurizing the pneumatic cylinder 162 to cause the shaft 164 to extend relative to the cylinder 162, against the spring bias, into a second, upward position (see FIG. 6). Releasing the trigger plate 172 will again connect the pneumatic cylinder 162 with the bleed line 178, thereby de-pressurizing the pneumatic cylinder 162 and permitting the shaft 164 and the movable platform 150 to return, under the force of the spring bias, to the first position.

As opposed to mounting the valve 170 on base plate 140 and operating it by means of the hand-operated trigger plate 172, cylinder 162 could be controlled by a valve placed on the floor and operated by a foot-operated trigger or plate. The valve of this embodiment is preferably a 3-way valve switch available from LINEMASTER Switch Corporation of Woodstock, Conn. (Cat. No. 3B-30A2-S).

Alternatively, the valve can be operated by a robot, a mechanical device, or the like. In an exemplary embodiment, the valve pneumatically actuates the movable platform 150 via pneumatic cylinder 162. It will be appreciated by those skilled in the art that the movable platform 150 can be actuated by a hydraulic system, electric motor, solenoid, or the like.

As explained in more detail above, the pneumatic cylinder 162 cooperates with the valve 170, and moves the platform 150 with respect to the stop surface 134 between the first and second positions. In the first position, the distance between the platform 150 and the stop surface 134 is greater than the axial length L of the filtration testing system 60. (See FIG. 3). This is illustrated in FIG. 5 in which the filtration testing system 60 is placed on the platform 150 with the shaft 164 of the actuating mechanism 160 in the downward position. Although it is preferred that the entire filtration testing system 60—including funnel 10, growth medium plate 30, lower cover plate 40, and upper cover plate 50—be placed on the platform 150, in order to simplify the drawings, growth medium plate 30, lower cover plate 40, and upper cover plate 50 are not explicitly shown in FIGS. 5 and 6.

In the second position, the distance between the platform 150 and the stop surface 134 is less than the axial length L of the funnel 10 and the growth medium plate 30 joined together prior to breaking the frangible connection 28 joining the filter ring 20 to the cup 12. This is illustrated in FIG. 6 in which the shaft 164 of the actuating mechanism 160 is in the upward position, the funnel 10 and the growth medium plate 30 combination is in contact with both the platform 150 and the stop surface 134, and the narrow portion 24 of the filter ring 20 is collapsed into the bottom 16 of the cup 12.

It will be appreciated that separation of the filter ring 20 and the cup 12 from each other is effected by an axial compressive force generated by relative movement of the moveable platform 150 toward the stop surface 134 with the funnel 10—with or without the growth medium plate 30, the upper cover plate 50, and the lower cover plate 40 joined thereto—disposed therebetween. It will be further appreciated that, in this regard, the housing 110 and the orientations of the platform 150 and the stop surface 134 play no roll in the generation of the axial force. That is, the housing could comprise any structure that will support the stop surface 134 in an opposed, spaced relationship with respect to the platform 150, and it is not necessary to the functioning of the device 100 that the housing include, e.g., the lower portion 112 and/or hood 122. Furthermore, the relative positions of the stop surface 134 and the platform 150 could be switched, with a moveable platform disposed above a stop surface. In such an arrangement, a dedicated stop surface could be omitted, and the platform could be supported a suitable distance above the base plate 140, with the base plate 140 functioning as a stop surface. Moreover, in such an arrangement, the filtration testing system 60 would be placed on the stop surface and the platform would be actuated in a downward motion until it contacts and applies the required axial force to the funnel. Alternatively, the filtration testing system 60 could be compressed between two spaced-apart surfaces that are each movable with respect to the other. As a still further alternative, the stop surface and the moveable platform could both be supported—e.g., by the base plate 140—in a horizontally spaced-apart relation. Such an arrangement would preferably include means for cradling the filtration funnel system 60 to keep it from rolling before being compressed.

Having described the structural and functional elements of the filter snapper device 100, a fluid contamination detection procedure employing the device 100 will be described.

After water has been passed through the filter 26, e.g., using the suction mechanism described above, of the filter ring 20, the funnel 10 is joined to the growth medium plate 30 such that the growth medium 32 is in contact with the filter 26. The upper cover plate 50 and the lower cover plate 40 are placed on the funnel 10 and the growth medium plate 30, respectively, and the funnel 10, with the growth medium plate 30 joined thereto, is then placed on and supported by the platform 150, which is in its first position, as shown in FIG. 5 Alternatively, the funnel 10 may be placed directly on the platform 150 prior to attaching the growth medium plate 30 to the filter ring 20. The funnel 10 is positioned on the platform 150 by a positioning fence 152 mounted to or formed on the platform 150. In the embodiment shown, positioning fence 152 is a curved, upstanding wall having a curvature generally conforming to that of the filter ring 20. The platform 150 is actuated by the valve 170 (via trigger plate 172), which supplies air under pressure into the pneumatic cylinder 162, thereby extending the shaft 164 and moving the platform 150 and the funnel 10 and growth medium plate 30 combination upward from the first position.

As illustrated in FIG. 6, the platform 150 continues to move the funnel 10 and associated growth medium plate 30 upward until a portion of the filtration testing system 60, e.g., the upper cover plate 50, engages or abuts against the stop surface 134. As the platform 150 continues to move upward toward the second position, an axial compressive force is applied to the testing system 60. The axial compressive force is sufficient to break the frangible connection 28 joining the filter ring 20 and the cup 12, thereby collapsing the narrow portion 24 of the filter ring into the bottom end 16 of the cup 12 (see FIG. 6). The axial compressive force is not, however, so great that the filter ring 20 or the growth medium plate 30 is damaged (e.g., cracked, warped, crushed, bent, etc.) in the process.

When the valve 170 is released (via trigger plate 172), air is permitted to escape the pneumatic cylinder 162 through the bleed line 178 and, consequently, the shaft 164 retracts into the cylinder 162 and the platform 150 returns to the first position so that the cup 12 and filter ring 20 components of the funnel 10 can be removed from the platform 150. The top cover plate 50 is placed on the open, upper end of the filter ring 20. The cup 12 can be disposed of in any suitable disposal means.

The growth medium plate 30 and associated filter ring 20 are then exposed to conditions sufficient to promote the biological growth of biological contaminants (e.g., bacteria or fungi) that may be present on the filter 26. For example, the growth medium plate 30 and associated filter ring 20 may be placed in an incubator at 37° C. for a set period of time or times and examined at the end of each period of time for changes, such as the appearance of colony forming units ("CFU"). If, based on this examination, there is an indication that the bioburden (i.e., the number of CFU) of the fluid sample is too high, then the source of the contaminated fluid can be disposed of before it is used in sterile laboratory or manufacturing procedures.

To destroy any biological contaminants that may have been deposited on the filter snapper device 100 during the procedure described above, the filter snapper device 100 is preferably washed at the completion of the procedure with a solution made up of 9 parts water and 1 part bleach, followed by a wash with 70% alcohol. Because of the corrosive nature of the bleach solution, the filter snapper device 100 is preferably made of electro polished 316 stainless steel. To facilitate cleaning, all housing joints are welded. To further facilitate cleaning, housing 110 is separated from base plate 140 by spacer elements 142 disposed between the base plate 140 and the bottom plate 118 of the housing 110. Spacer elements 142 are preferably formed from Delrin® acetyl resin. Similarly, the actuating mechanism 160 is separated from the bottom of the housing 110 by means of spacers 166—preferably formed from stainless steel—disposed between the bottom plate 118 and the actuating mechanism 160. Finally, feet 144—preferably formed from a non-skid elastomer—are disposed on the bottom of the base plate 140 to provide a separation between the base plate 140 and a surface upon which the filter snapper device 100 may be supported.

The foregoing has described the principles, embodiments, and modes of operation of the present invention. However, the invention should not be construed as being limited to the particular embodiments described above, as they should be regarded as being illustrative and not as restrictive. It should be appreciated that variations may be made in those embodiments by those skilled in the art without departing from the scope of the present invention.

Modifications and variations of the present invention are possible in light of the above teachings. It is therefore to be understood that the invention may be practiced otherwise than as specifically described herein.

What is claimed is:

1. A device for applying an axial compressive force to a fluid contamination detection system comprising a funnel having first and second members joined to each other by a frangible connection, said device comprising:
   a stop element;
   a platform supported relative to a base and disposed in an opposed, spaced-apart relationship relative to said stop element, wherein said platform is movable relative to said stop element between (i) a first position in which the distance between said platform and said stop element is greater than the axial length of the detection system when the first and second members are connected to each other, and (ii) a second position in which the distance between said platform and said stop element is less than the axial length of the detection system when the first and second members are connected to each other;
   a housing containing said stop element and said platform, wherein said housing has a generally triangular hood; and
   an actuating mechanism for causing movement of said platform between said first and second positions,
   wherein said platform is movable from said first position to said second position during which movement a portion of a detection system disposed between said stop element and said platform contacts said stop element, resulting in an axial compressive force sufficient to break the frangible connection joining said first and second members of the funnel without damaging at least one of the first and second members of the funnel.

2. The device of claim 1, wherein said actuating mechanism comprises a valve and a pneumatic cylinder.

3. The device of claim 2, wherein said valve can be manually operated.

4. The device of claim 1, further comprising a support structure joining said base to said stop element.

5. The device of claim 4, wherein said support structure comprises said housing.

6. The device of claim 1, wherein said housing is an open structure.

7. The device of claim 1, wherein said housing is made of stainless steel.

8. The device of claim 1, wherein said housing is mounted to said base.

9. The device of claim 1, further comprising a positioning structure disposed on said platform and constructed and arranged to position the detection system on said platform.

10. A filter snapper system comprising a fluid contamination detection system comprising a funnel having first and second members joined to each other by a frangible connection in combination with said device of claim 1.

11. The system of claim 10, wherein said second member of said funnel includes a filter.

12. The system of claim 11, wherein said first member of said funnel is configured to hold a fluid.

13. The system of claim 11, wherein said detection system further comprises a growth medium plate attached to said second member of said funnel in such a manner that a growth medium contained within said growth medium plate is in contact with said filter.

14. The system of claim 10, wherein said actuating mechanism comprises a valve and a pneumatic cylinder.

15. The system of claim 14, wherein said valve can be manually operated.

16. The system of claim 10, wherein said device further comprises a support structure joining said base to said stop element.

17. The system of claim 10, wherein said housing is an open structure.

18. The system of claim 10, wherein said housing is mounted to said base.

* * * * *